(12) United States Patent
Zhdaneev et al.

(10) Patent No.: US 8,013,295 B2
(45) Date of Patent: Sep. 6, 2011

(54) ION MOBILITY MEASUREMENTS FOR FORMATION FLUID CHARACTERIZATION

(75) Inventors: Oleg Zhdaneev, Cambridge, MA (US); Gordon Lambertus, Wellesley, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 230 days.

(21) Appl. No.: 12/275,589

(22) Filed: Nov. 21, 2008

(65) Prior Publication Data
US 2010/0127163 A1    May 27, 2010

(51) Int. Cl.
B01D 59/44    (2006.01)
H01J 49/00    (2006.01)
H01J 49/26    (2006.01)

(52) U.S. Cl. ......... 250/288; 250/281; 250/282; 250/287
(58) Field of Classification Search ............ 250/288, 250/281, 282, 287
See application file for complete search history.

(56) References Cited

U.S. PATENT DOCUMENTS

| | | | |
|---|---|---|---|
| 4,855,595 A | 8/1989 | Blanchard | |
| 5,166,747 A | 11/1992 | Schroeder et al. | |
| 5,218,203 A | 6/1993 | Eisele et al. | |
| 6,925,392 B2 | 8/2005 | McNeil, III et al. | |
| 7,176,453 B2 | 2/2007 | Miller et al. | |
| 7,241,989 B2 | 7/2007 | Miller et al. | |
| 7,355,170 B2 * | 4/2008 | Miller et al. | 250/287 |
| 7,365,316 B2 | 4/2008 | Miller et al. | |
| 7,397,027 B2 | 7/2008 | Li | |
| 7,429,729 B2 | 9/2008 | Schultz et al. | |
| 7,535,329 B2 | 5/2009 | Gorshkov | |
| 7,576,319 B2 * | 8/2009 | Miller et al. | 250/282 |
| 7,696,474 B2 | 4/2010 | Wu et al. | |
| 7,714,284 B2 * | 5/2010 | Miller et al. | 250/295 |
| 2010/0127163 A1 | 5/2010 | Zhdaneev et al. | |

OTHER PUBLICATIONS

Brunnee, Curt "Review: The Ideal Mass Analyzer: Fact or Fiction?" International Journal of Mass Spectrometry and Ion Processes, 76, (1987) pp. 125-237.

Buryakov et al, "A new method of separation of multi-atomic ions by mobility at atmospheric pressure using a high-frequency amplitude-asymmetric strong electric field", International Journal of Mass Spectrometry and Ion Processors, 128 (1993) pp. 143-148.

Kendler et al, "Fragmentation pathways and mechanisms of aromatic compounds in atmospheric pressure studied by GC-DMS and DMS-MS", ScienceDirect, International Journal of Mass Spectrometry, 263 (2007) pp. 137-147.

(Continued)

*Primary Examiner* — Nikita Wells
(74) *Attorney, Agent, or Firm* — Brigid Laffey; Rachel Greene; Helene Raybaud

(57) ABSTRACT

Methods and related apparatuses for chemically analyzing at least one sample of fluid, such that a gas flow of at least one fluid sample is directed into a mixing region of an ion mobility device, wherein the mixing region is in communication with at least one container having at least one other fluid. Further, creating an ion flow of gaseous ions, a mixture of gaseous ions or a gaseous neutral species from the at least one sample and the at least one other fluid. Further still, injecting the ion flow from the mixing region into at least one ion mobility assembly of the ion mobility device, the at least one ion mobility assembly comprising at least one mobility tube; and, detecting the ions from the ion flow exiting the ion mobility assembly.

56 Claims, 9 Drawing Sheets

OTHER PUBLICATIONS

Lambertus et al, "Silicon Microfabricated Column with Microfabricated Differential Mobility Spectrometer for GC Analysis of Volatile Organic Compounds", Anal. Chem. 2005, vol. 77, No. 23, pp. 7563-7571.

Lawrence et al, "Detection of Ethylene Glycol Dinitrate Vapors by Ion Mobility Spectrometry Using Chloride Reagent Ions", Anal. Chem., 1988, vol. 60, pp. 104-109.

Revercomb et al, "Theory of Plasma Chromatography/Gaseous Electrophoresis—A Review", Analytical Chemistry, vol. 47, No. 7, Jun. 1975, pp. 970-983.

Clemmer et al, "Ion mobility measurements and their applications to clusters and biomolecules", Journal of Mass Spectrometry, vol. 32, pp. 577-592, (1997).

Eiceman et al, Ion Mobility Spectrometry, Second Edition, CRC Press, pp. 25-28 and 136, 2005.

Marmarelis et al, Analysis of Physiological Systems, Plenum Press, New York/London, pp. 188-195, 1978.

Eiceman, "Detection of Microorganisms and Related Chemical Compounds Using Ion Mobility Spectrometry", Final Report on Prime Contract DAAA15-90-C-1006, Subcontract Gc-2192-91-002: Aug. 10, 1993; New Mexico State University, Las Cruces, NM.

* cited by examiner

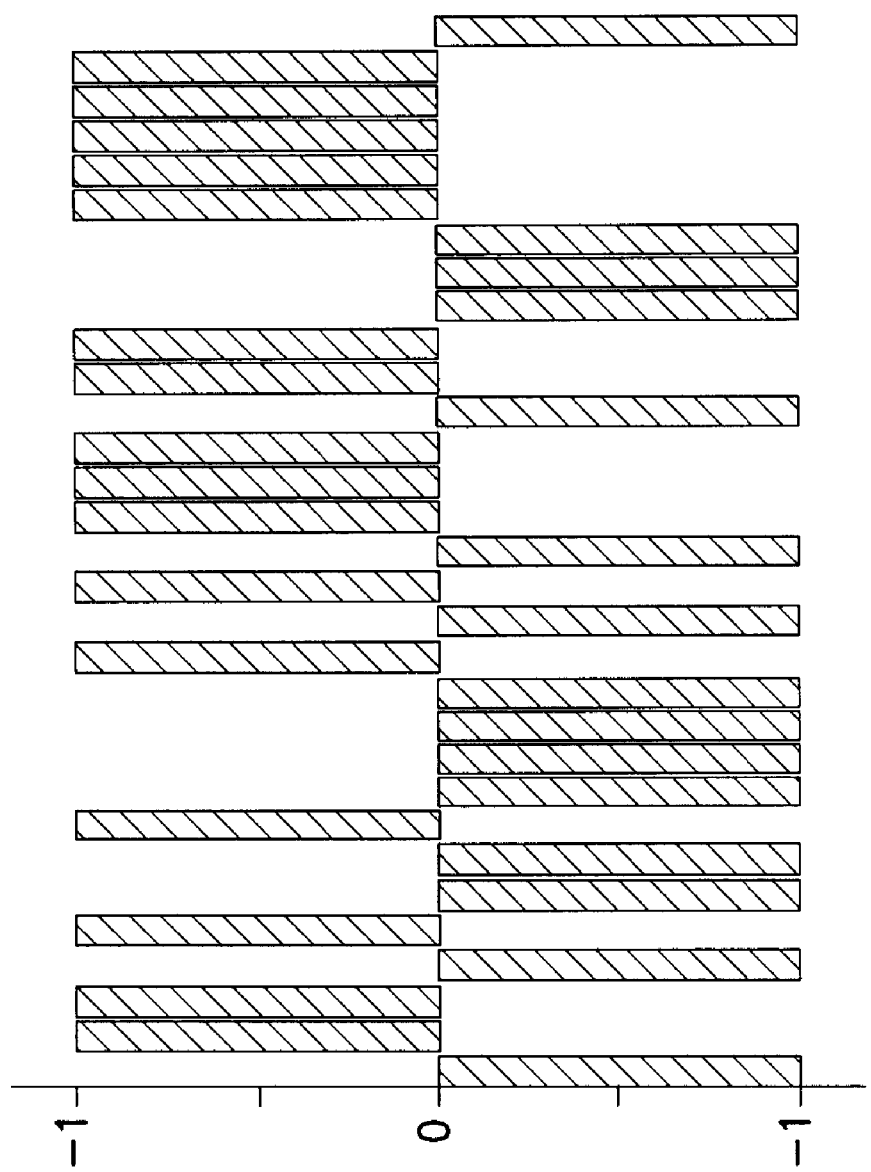
FIG.6
M SEQUENCE OF LENGTH 31

ION MOBILITY MEASUREMENTS FOR FORMATION FLUID CHARACTERIZATION

BACKGROUND OF THE INVENTION

1. Field of the Invention

This invention generally relates to methods and devices of chemical analysis of fluids and gases. In particular, utilizing ion mobility techniques for detecting and identifying components of interest in a fluid mixture such as in a formation fluid.

2. Background of the Invention

In the field of chemical analysis the use of ion mobility spectrometers have been widely used. Ion mobility spectrometers separate ionic species based on their ion mobility in a given media (either gas or liquid). For example, several approaches to chemical identification are based on the recognition that ion species have different ion mobility characteristics under different electric field conditions at atmospheric pressure. These approaches include time-of-flight Ion Mobility Spectrometry (IMS) and differential mobility spectrometry (DMS), the latter also known by other names such as field asymmetric ion mobility spectrometry (FAIMS). Ion mobility measurements have been widely used for identification of components including but not limited to drugs, explosives, and chemical warfare agents [Eiceman. G. A., Karpas Z., *Ion Mobility Spectrometry, CRC Press,* 2005].

In a conventional time-of-flight Ion Mobility Spectrometry (IMS) device, a weak DC field gradient is established between an upstream electrode and a downstream collector electrode and then an ionized sample is released into the DC field. The ionized sample flows toward the collector electrode. Ion species are identified based on the time of flight of the ions to the collector. The DC field is weak where ion mobility is constant. In other words, the IMS spectrometers separate ions based on their steady state ion mobilities under constant electric field. More recently, improvements have been reported in the lower limits of detectability for ion mobility instruments. In U.S. Pat. No. 5,218,203 a device is disclosed for restricting a sample gas from entering the drift region and limiting sample gas ions to such regions. However, there are several limitations of convention IMS spectrometers instruments: first, they require high resolving power for operation; and secondly, the drift tubes used in the IMS devices are still comparatively large and expensive and suffer from losses in detection limits when made small. The search therefore still continues for a successful field instrument that includes both a small ion injector/column and a small detector/spectrometer and yet is able to rapidly produce unambiguous orthogonal data for identification of a detected compound.

A typical differential mobility spectrometry (DMS) device includes a pair of opposed filter electrodes defining an analytical gap between them in a flow path (also known as a drift tube or flow channel). Ions flow into the analytical gap. A compensated high-low varying asymmetric RF field (sometimes referred to as a filter field, a dispersion field or a separation field) is generated between the electrodes transverse the ion flow in the gap. Field strength varies as the applied RF voltage (sometimes referred to as dispersion voltage, separation voltage, or RF voltage) and size of the gap between the electrodes. Also, ions are displaced transversely by the DMS filter field, with a given species being displaced a characteristic amount transversely toward the electrodes per cycle. DC compensation is applied to the electrodes to compensate or offset the transverse displacement generated by the applied RF for a selected ion species. The result is zero or near-zero net transverse displacement for that species, which enables that species to pass through the filter for downstream processing such as detection and identification. Other ions undergo a net transverse displacement toward the filter electrodes and will eventually undergo collisional neutralization on one of the electrodes. Both the typical DMS and IMS devices separate the ions through the use of nonlinear mobility, which occurs at high values of normalized electric field. The normalized electric field refers to the relation between the applied electric field at a given location in space divided by the neutral particle number density. The normalized electric field is a key parameter in ionized gases and plasmas, as the energy of ionized particles, the breakdown and sustaining voltages and other key parameters depend upon this ratio. The DMS devices have sensitivity and selectivity that are still substantially worse (less) than linear drift tubes. Further, such systems typically operate at atmospheric pressure.

However, at least one limitation of convention DMS systems is that the compensation voltage applied to the filter electrodes typically generates fringe fields that force ions to impact and deposit charge along the flow path of the system adjacent to the filter. As the ions deposit their charge, a charge build up occurs that counteracts the influence of the fringe fields and allows for subsequent stable ion detection. Unfortunately, the period of time in which the DMS system reaches stable ion detection introduces response time delays, especially in a system performing multiple sample detections, which may reduce the speed and responsiveness of current DMS systems. Also, the dependence on a charge build up to enable stable ion detection may adversely affect the stability and sensitivity of the DMS system where the charge build up is dependent on other variable factors such as surrounding environmental conditions.

Moreover, in many cases, in a less-than ideal operating surface environments (in particular those with high humidity, temperature or other site-specific interferences), the above noted spectrometers, e.g., IMS, DMS or FAIMS, performance is significantly limited. The performance of the ion mobility spectrometers in these circumstances can be improved by increasing the temperature of the gas. High temperature ion mobility spectrometers are common in applications that require high resolution analysis, such as explosive detection. Unfortunately, the use of high temperature drift tubes in differential mobility spectrometer devices results in high power consumption, limited portability and other operational disadvantages, including slow turn-on from cold conditions. In addition, dry drift gas is often required in these types of spectrometers. A dehumidifier in front of the unit has been used to address these problems (either as a water absorber or as a hydrophobic membrane) with significant trade-offs. The volume and weight, as well as the need for regeneration, makes the use of dehumidifier cell impractical, while the use of the hydrophobic membrane decreases the volume/amount of the sample that is introduced into the device, decreases its sensitivity.

Therefore, there is a need to develop a spectrometer that could overcome at least some of the above noted limitations over the known spectrometers.

SUMMARY OF THE INVENTION

According to embodiments of the invention, the invention can include a method for chemically analyzing at least one sample of fluid. The method comprises the steps of: (a) directing a gas flow of the at least one fluid sample into a mixing region of an ion mobility device, wherein the mixing region is in communication with at least one container having at least one other fluid. The method further includes the step of (b)

creating an ion flow of gaseous ions, a mixture of gaseous ions or a gaseous neutral species from the at least one sample and the at least one other fluid. Finally, the method of the invention includes the step of (c) injecting the ion flow from the mixing region into at least one ion mobility assembly of the ion mobility device, the at least one ion mobility assembly comprising at least one mobility tube; and, detecting the ions from the ion flow exiting the ion mobility assembly.

According to an aspect of the invention, the method can include the at least one sample of fluid that is collected from one or more inlet location where the fluids originated. Further, the method can provide for the ion mobility device having one or more sampling chamber. The at least one fluid sample may be directed into the one or more sampling chamber of the ion mobility device wherein the one or more sampling chamber provides for the at least one fluid sample to be put in a gaseous phase so as to create the gas flow of step (a). Further, the at least one device can be structured and arranged between the at least one sample chamber and the mixing region, such that the at least one device is from the group consisting of one of a separation system, a non-destructive sensor, a mass spectrometer, another ion mobility device, or some combination thereof. Further still, the separation system includes one of a liquid chromatography, a gas chromatography, a size exclusion chromatography system, or some combination thereof.

According to an aspect of the invention, the method can include the at least one other fluid to consist of one or more drift gas, wherein the one or more drift gas is from the group consisting of one of nitrogen, helium, air, argon, water vapor, one or more organic molecules, one or more inorganic molecules or any combination thereof. Further, the at least one sample and the at least one other fluid can be ionized from a group consisting of one of a flux of electrons from a radioactive source, by high energy photons with an energy higher than 12.8 eV, a gas discharge device, an ion flux system, a field ionization assembly, a penning ionization process, a chemical ionization assembly, a dissociative ionization assembly, a collision induced ionization assembly or some combination thereof. It is possible the at least one ion mobility assembly includes a top electrode and a bottom electrode, such that ion flow is injected into a filter region of the at least one mobility tube by one of orthogonally or parallel in relation to an axis of the bottom electrode.

According to an aspect of the invention, the method can include the at least one mobility tube that has a filter region comprising of two or more electrodes along with at least one inlet positioned on an end of the at least one mobility tube. The filter region can have a filter geometry wherein two electrodes of the two or more electrodes are spaced apart from each other, such that an inlet cross-section is greater than an exit cross-section. The filter region can have a filter geometry wherein two electrodes of the two or more electrodes are spaced apart from each other, such that an inlet cross-section is less than an exit cross-section. The filter region may have a filter geometry wherein two electrodes of the two or more electrodes are non-uniformly spaced apart from each other, such that an inlet cross-section is greater than an exit cross-section. The filter region can have a filter geometry wherein at two electrodes of the two or more electrodes are non-uniformly spaced apart from each other, such that an inlet cross-section is less than an exit cross-section. It is also possible the at least one mobility tube can include at least one inlet positioned between a first end and a second end of the at least one mobility tube, wherein the filter region has a filter geometry wherein two electrodes of the two or more electrodes are uniformly spaced apart from each other.

According to an aspect of the invention, the method can include the at least one mobility tube having a filter region, such that the filter region is positioned downstream from step (c) or an ionization region. Further, the at least one ion mobility assembly can simultaneously detects ions of both negative and positive polarities. It is also possible that the at least one sample and the at least one other fluid are ionized, after ionization a plurality of negative and positive ions accelerate in at least two electric fields according to their respective ion polarities and are detected on opposite sides of at least one mobility tube of the plurality of mobility tubes.

According to an aspect of the invention, the method can include the ion mobility device having two or more ion mobility assemblies. Further, the at least one ion mobility assembly may have two or more detectors. Further still, the at least one fluid from the fluids can be from the group consisting of one of a formation fluid mixture or a fluid from an oilfield application. It is also possible the fluids can be one of formation fluids or fluids from the mixing region or some combination thereof. The formation fluids can be from a group consisting of one of water, crude oil, drilling mud, gases or any combination thereof. Further, the fluids from the mixing region may be from the group consisting of one of gases, inorganic dopant, organic dopant, water vapor or any combination thereof. Further still, the ion mobility device can be from the group consisting of one of a ion mobility spectrometry or a differential ion mobility spectrometry.

According to an aspect of the invention, the method can include recording the results of the detected ions by the at least one ion mobility assembly into a processor as an ion mobility spectral profile data, and then inputting other measured data from other well log systems into the processor. Further, analyzing the combination of the ion mobility spectral profile data with the other measured data by conducting one of a quantitative analysis, a qualitative analysis or both a quantitative and qualitative analysis so as to provide reliable reservoir evaluation information for making a decision in relation to oilfield applications.

According to embodiments of the invention, the invention can include a method for chemical analysis of fluids from an oilfield application such as a reservoir. The method comprises of the step of (a) collecting at least one sample of fluid from one or more inlet location where the fluids originated, and an ion mobility device having one or more sampling chamber and at least one ion mobility assembly. Further, the step of (b) directing the at least one fluid sample into the one or more sampling chamber of the ion mobility device wherein the one or more sampling chamber provides for the at least one fluid sample to be put in a gaseous phase so as to create a gas flow. Further still, the step of (c) directing the gas flow of the at least one fluid sample into a mixing region of the ion mobility device, wherein the mixing region is in communication with at least one container having at least one other fluid. The step of (d) creating an ion flow of gaseous ions, a mixture of gaseous ions or a gaseous neutral species from the at least one sample and the at least one other fluid. Finally, the method includes step (e) injecting the flow from the mixing region into the at least one ion mobility assembly of the ion mobility device, the at least one ion mobility assembly comprising at least one mobility tube; and, detecting the ions from the flow exiting the at least one ion mobility assembly.

According to embodiments of the invention, the invention can include a ion mobility device. The ion mobility device comprises of a mixing region than can be in fluid communication with a first fluid of at least one fluid sample and one or more container having at least one other fluid, such that the first fluid can be mixed with the at least one other fluid.

Further, the ion mobility device can include a source for generating a flow of gaseous ions, a mixture of gaseous ions or a gaseous neutral species from the at least one fluid sample and the at least one other fluid. Further still, at least one ion mobility assembly fluidly connected to the source, the at least one ion mobility assembly comprising at least one mobility tube and at least one detector, wherein the at least one ion mobility assembly is detecting ions from an ion flow exiting the ion mobility assembly.

According to an aspect of the invention, the ion mobility device can include the first fluid of the at least one fluid sample that is in fluid communication with one or more sample chamber. Further, the one or more sample chamber can provide for the first fluid of the at least one fluid sample to be put in a gaseous phase so as to create a gas flow. Further still, the at least one other fluid consists of one or more drift gas, wherein the one or more drift gas is from the group consisting of one of nitrogen, helium, air, argon, water vapor, one or more organic molecules, one or more inorganic molecules or any combination thereof. It is possible, the at least one mobility tube includes a filter region comprising of two or more electrodes along with at least one inlet positioned on an end of the at least one mobility tube.

According to an aspect of the invention, the ion mobility device can include the filter region having a filter geometry wherein two electrodes of the two or more electrodes are spaced apart from each other, such that an inlet cross-section is greater than an exit cross-section. Further, the filter region can have a filter geometry wherein two electrodes of the two or more electrodes are spaced apart from each other, such that an inlet cross-section is less than an exit cross-section. Further still, the filter region can have a filter geometry wherein two electrodes of the two or more electrodes are non-uniformly spaced apart from each other, such that an inlet cross-section is greater than an exit cross-section. It is possible the filter region can have a filter geometry wherein two electrodes of the two or more electrodes are non-uniformly spaced apart from each other, such that an inlet cross-section is less than an exit cross-section. The at least one mobility tube may include at least one inlet positioned between a first end and a second end of the at least one mobility tube, wherein the filter region can have a filter geometry wherein two electrodes of the two or more electrodes are uniformly spaced apart from each other. Further, the at least one mobility tube can include a filter region, such that the filter region is positioned downstream from step (c) or the ionization region.

According to an aspect of the invention, the ion mobility device can include the at least one ion mobility assembly having a top electrode and a bottom electrode, such that ion flow is injected into a filter region of the at least one mobility tube by one of orthogonally or parallel in relation to an axis of the bottom electrode. Further, at least one device is structured and arranged between the at least one sample chamber and the mixing region, such that the at least one device is from the group consisting of one of a separation system, a non-destructive sensor, a mass spectrometer, another ion mobility device, or some combination thereof. Further still, the separation system includes one of a liquid chromatography, a gas chromatography, a size exclusion chromatography system, or some combination thereof. It is possible, the at least one ion mobility assembly simultaneously detects ions of both negative and positive polarities. The ion mobility device can have two or more ion mobility assemblies. Further, the at least one ion mobility assembly may have two or more detectors.

According to an aspect of the invention, the ion mobility device can include the at least one ion mobility device to use a plurality of electrostatic fields to focus ion flux in the at least one mobility tube to effect a peaks resolution and a signal to noise ratio. Further, the at least one ion mobility device includes at least one magnetic field that is used for ion flux manipulation to improve one or more component of interests resolutions in the analyzable mixture of the first fluid with the at least one other fluid. It is possible a m-sequence ion injection can be used to enhance a signal to noise ratio and resolution between the one or more components of interests in ion mobility measurements. Further, the at least one ion mobility device can include multiplexing ion mobility spectrometry cells, such that an array of sensors are arranged in parallel rather in series, along with the at least one sample being introduced as a continuous flow to an ionization source, a filter region, and a plurality of collectors as the at least one sample is transported by means of a transfer gas. Further still, ion mobility device is from the group consisting of one of a ion mobility spectrometry or differential ion mobility spectrometry. It is possible for the ion mobility device to operate above an ambient pressure. Further, the at least one ion mobility assembly can have one or more electric field, such that the one or more electric field oscillating is with one of one or more maximum pulses, one or more minimum pulses or both.

According to embodiments of the invention, the invention can include a system for chemical analysis of fluids from an oilfield application such as a reservoir. The system comprises of (a) collecting at least one sample of fluid from one or more inlet location where the fluids originated, and an ion mobility device having one or more sampling chamber and at least one ion mobility assembly. Then, (b) directing the at least one fluid sample into the one or more sampling chamber of the ion mobility device wherein the one or more sampling chamber provides for the at least one fluid sample to be put in a gaseous phase so as to create a gas flow. Further, (c) directing the gas flow of the at least one fluid sample into a mixing region of the ion mobility device, wherein the mixing region is in communication with at least one container having at least one other fluid. Then, (d) creating an ion flow of gaseous ions, a mixture of gaseous ions or a gaseous neutral species from the at least one sample and the at least one other fluid. Finally, (e) injecting the flow from the mixing region into the at least one ion mobility assembly of the ion mobility device, the at least one ion mobility assembly comprising at least one mobility tube; and, detecting the ions from the flow exiting the at least one ion mobility assembly.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 6 shows at least one embodiment that addresses the utilization of M-sequence for ion-mobility measurements, according to embodiments of the invention;

DETAILED DESCRIPTION OF THE PREFERRED EMBODIMENTS

Figure 1:
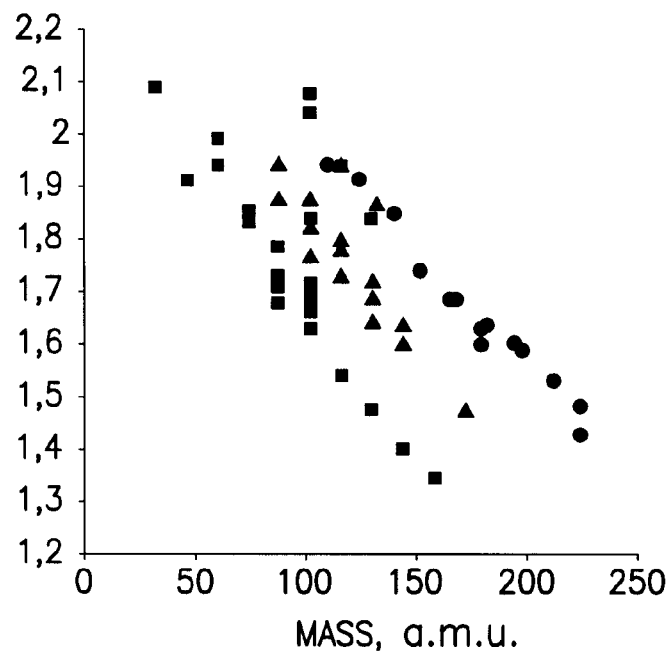
FIG. 1 shows reduced mobility coefficients versus mass of drifted components, wherein alcohols are representative as a square shape (□), esters representative as a triangle shape (□), and organophosphates representative as a circle shape (□) (see the G. A. Eiceman Final Report, in Geocenter, Inc., Aug. 10, 1993)

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

The According to embodiments of the invention, the invention can include a method for chemically analyzing at least one sample of fluid. The method comprises the steps of: (a) directing a gas flow of the at least one fluid sample into a mixing region of an ion mobility device, wherein the mixing region is in communication with at least one container having at least one other fluid. The method further includes the step of (b) creating an ion flow of gaseous ions, a mixture of gaseous ions or a gaseous neutral species from the at least one sample and the at least one other fluid. Finally, the method of the invention includes the step of (c) injecting the ion flow from the mixing region into at least one ion mobility assembly of the ion mobility device, the at least one ion mobility assembly comprising at least one mobility tube; and, detecting the ions from the ion flow exiting the ion mobility assembly.

According to embodiments of the invention, the invention can include a ion mobility device. The ion mobility device comprises of a mixing region than can be in fluid communication with a first fluid of at least one fluid sample and one or more container having at least one other fluid, such that the first fluid can be mixed with the at least one other fluid. Further, the ion mobility device can include a source for generating a flow of gaseous ions, a mixture of gaseous ions or a gaseous neutral species from the at least one fluid sample and the at least one other fluid. Further still, at least one ion mobility assembly fluidly connected to the source, the at least one ion mobility assembly comprising at least one mobility tube and at least one detector, wherein the at least one ion mobility assembly is detecting ions from an ion flow exiting the ion mobility assembly.

According embodiments of the invention, the invention includes methods and devices for disclosing a novel approach for chemical composition analysis of formation fluids in a downhole/surface environment, including but not limited to the light hydrocarbons (gases), $H_{2S}$, and others. However, the present embodiments of the invention are not limited to subterranean environments but may also include surface environments. The embodiments of the invention utilize the ion mobility technique for mixture analysis. Embodiments of the invention consist of two parts, hardware embodiments along with methods of measurements. The hardware components may consist of a sampling system, an ionization chamber, an electrical field generator, a magnetic field generator, a drift chamber, at least one detector, a pre-separation device, a gas supply system, among other things. The operating software can include at least one algorithm and database to quantitatively identify components in the mixture.

According embodiments of the invention, the invention methods and devices can be capable of real-time formation fluids characterization at downhole conditions, and could be implemented on different platforms (wireline, logging while drilling, testing, etc) utilizing different types of conveyance (wireline cable, drilling tubing, coil tubing, tractor). It is also noted that along with downhole conditions, surface conditions can also be considered. Further, the invention the methods and devices can be an improvement over conventional methods that require samples to be brought to surface facilities for analysis and/or limited to optical spectroscopy. The data obtained by at least one embodiment of the invention could be combined with other logging data like gas chromatography, optical measurements, and mass spectrometry. Embodiments of the invention can utilize chemical and electron ionization from different sources.

Time-of-flight Ion Mobility Spectrometry (IMS) and differential mobility spectrometry (DMS) provide for selective marker-free identification of molecules and molecular aggregates in a mixture that can be used as a detector for gas/liquid chromatography and other compositional analysis systems like a mass spectrometry. Embodiments of this invention may also be coupled with a pre-separation apparatus such as GC or LC as well as with a device for accurate component identification like MS. To improve the ion separation the ion mobility spectrometers could be combined in a tandem like IMS-IMS, IMS-DMS and so on.

Overview of the Mobility Spectrum

Referring to FIG. 1, a mobility spectrum can contain all the information provided by a mobility measurement. This includes the mobility coefficients (characteristic of an ion), peak shape (characteristic of the drift tube), and ion fragmentation (characteristic of a chemical class). Mobility coefficients are governed by size to charge ratio and the reduced mass of the ion in the atmosphere of analysis and could be used for the identification of the components of interest (see for example table 1 below and FIG. 1) especially in combination with gas chromatography (GC), liquid chromatography (LC), and mass spectrometry (MS). FIG. 1 shows reduced mobility coefficients versus mass of drifted components, wherein alcohols are representative as a square shape (□), esters are representative as a triangle shape (Δ), and organophosphates are representative as a circle shape (O) (see Eiceman, G. A., *Final Report, Geocenters, Inc., Subcontract GC-2192-91-002, Prime contract DAAA15-90-C-1006*, Aug. 10, 1993).

Differential mobility spectrometry was first introduced in the early 90s as Field Ion Spectrometry (Buryakov, I. A., Krlov, E. G., Nazarov, E. G. Rasulev, U. K., *Int. J. Mass. Spectrom. Ion Processes*, 1993, 128, 143-148). The theory of ion separation that was described in this earlier work proved to operate under several different modes including the use of cylindrical electrodes in a commercialized instrument by Ionalytics Corporation, which was later bought out by Thermo, and a micro-machined parallel plate version later commercialized by Sionex Corporation. These instruments were based on the same ion separation mechanisms, while incorporating differing ionization methods, electrode geometries, and collector plate geometry. The Sionex DMS is a microfabricated detector with electrode dimensions of 15 mm×1.5 mm with a gap of 0.5 mm. When housed with an onboard EPC and electronics the whole unit is just about 4-in wide by 6-in long by 2-in high.

TABLE 1

| CLASS | COMPOUNDS | Molecular Weight (amu) | K cm²/Vs |
|---|---|---|---|
| Alkanes | n-Pentane | 72 | 2.04 |
| | n-Hexane | 86 | 2.02 |
| | n-Heptane | 100 | 1.92 |
| | n-Octane | 114 | 1.82 |
| | n-Nonane | 128 | 1.73 |
| | n-Decane | 142 | 1.64 |
| Cyclo-Alkanes | Cycloheptane | 98 | 1.97 |
| | Methylcyclohexane | 98 | 1.96 |
| | Ethylcyclopentane | 98 | 1.95 |
| | Ethylcyclohexane | 112 | 1.87 |
| | Isopropylcyclohexane | 126 | 1.79 |
| | Propylcyclohexane | 126 | 1.78 |
| | Cyclodecane | 140 | 1.73 |
| | Butylcyclohexane | 140 | 1.68 |
| Alkenes | Cyclohexene | 82 | 1.83 |
| | 1-Hexene | 84 | 1.83 |
| | 5-Methylhexene-2 | 98 | 1.96 |
| | 2-Heptene | 98 | 1.95 |
| | Octene | 112 | 1.83 |
| Aromatics | Benzene | 78 | 1.96 |
| | Toulene | 92 | 1.89 |
| | Styrene | 104 | 2.04 |

Table 1 illustrates example of mobility coefficients obtained experimentally [Eiceman, G. A., *Final Report, Geocenters, Inc., Subcontract GC-2192-91-002, Primecontract DAAA15-90-C-1006*, Aug. 10, 1993]

DESCRIPTION OF EMBODIMENTS OF THE INVENTION

Spectrometry techniques currently implemented in formation fluid analysis have a limited ability to resolve the presence of different components in a complex mixture. For example, when utilizing ion mobility spectrometry it is possible to distinguish between the components in the formation mixture, and then separate and identify them with a proper spectral library. It is also noted that implementation of ion mobility methods of analysis could significantly improve the logging while drilling measurements due to the extremely fast response of these measurements. This could be utilized for identification of components of interest while drilling (e.g. methane).

The components of ion mobility analysis system can be grouped into several main categories:
  Ionization sources for ionization of sample components,
  Drift tube components where ions are separated based on their mobility,
  Detectors, that detect ions,
  signal analyzers, and
  software that utilize the detector signal, control communication between system and user, and comparison to the user spectral library for identification of the components of interest.

Figure 2:
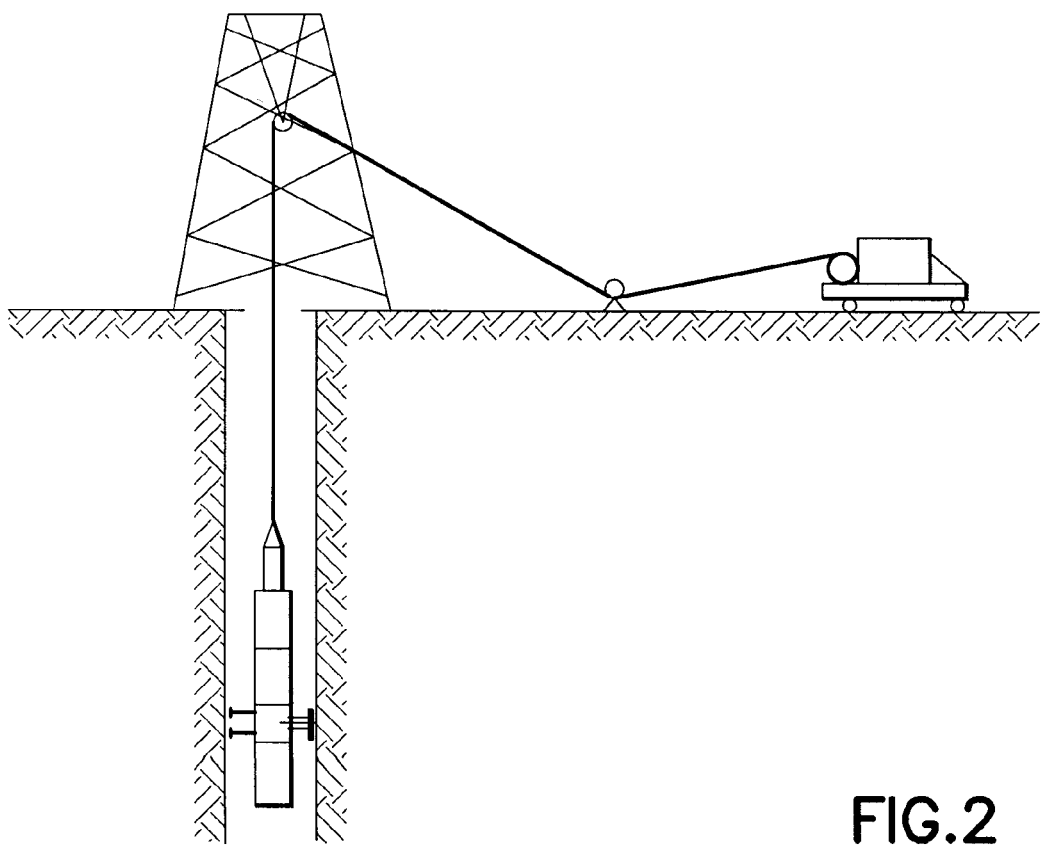
FIG. 2 shows a small quantity of the formation fluid extracted from a reservoir using a sampling tool (see R. J. Schroeder and J. A. Tarvin, U.S. Pat. No. 5,166,747)

According to embodiments of the invention, and referring to FIG. 2, the invention methods and devices describe at least one implementation of mobility spectrometry for downhole formation fluid analysis and or for surface fluid analysis. Referring to the diagram in FIG. 2, a small quantity of the formation fluid is extracted from a reservoir using a sampling tool [Schroeder, R. J., Tarvin, J. A., Apparatus and Method for Analyzing the Composition of Formation Fluids, U.S. Pat. No. 5,166,747 (1992).]. Then, the formation fluid after preliminary filtering, e.g. to remove sand particles via a sampling tool flowline, is delivered to the module where an ion mobility spectrometer is placed. The liquid or gas is allowed to expand and evaporate in a sample chamber that is roughly one million times the volume of the extracted fluid. In one embodiment of the tool there are multiple sample chambers, which are isolated from each other by valves. After expansion a valve, e.g. a piezo-electric leak valve, is opened into the ionization region of the drift chamber where the sample gases are ionized either by photons, electrons, ions, or by interaction with exited reactant particles. The molecular ions or fragments travel into the drift chamber under an electrical field gradient where they are separated on the basis of their mobility coefficients. After separation in the drift chamber the ions reach the detector, which can consist of a Faraday cup.

A differential mobility spectrometry (DMS) consists of nominally the same components as the ion mobility spectrometer previously described, i.e. an ionization source, a drift tube region, detectors, signal analyzers, and the interface software. In the case of a DMS, however, a sample will be introduced as a continuous flow to the ionization source, the filter region, and the collectors as it is transported by means of a transfer gas.

Variation of Drift Gases Downhole/Surface

The average velocity of the ion $v_d$ in the gas is directly proportional to the electric field intensity E in case of low field $$v_d = K \cdot E, \qquad \text{Eq. (1)}$$

where K is the mobility coefficient, and varies as a square root of electric field in case of strong fields. For low field setup $(M \cdot v_d^2/3 \cdot k \cdot T \ll 1)$ [Revercomb H. E.; Mason, E. A. "*Theory of Plasma Chromatography/Gaseous Electrophoresis: A Review*", Anal. Chem. 1975, 47, 970-983] the mobility coefficient could be evaluated using the following equation:

$$K = \frac{3 \cdot q}{16 \cdot N} \cdot \left( \frac{2 \cdot \pi}{k \cdot T} \cdot \left( \frac{1}{m} + \frac{1}{M} \right) \right)^{1/2} \cdot \frac{1}{\Omega}, \qquad \text{Eq. (2)}$$

where q is the ion charge, N is the density of the drift gas, m is the ion mass, M is the mass of the neutral particle, k is the Boltzmann constant, T is the temperature of the drift gas, and Ω is the collision cross-section of the ion neutral particle ($\approx \pi \cdot d^2$, where d is the sum of the ion and neutral particle radii).

One of the parameters in the system that can potentially have a significant effect on the analytical results is the type of the drift gas. The drift gas determines the sort of reagent ion and complex formation that will be produced in the ionization part of the device. Omitting the plasma chemical interaction in the ionization part of the device the effect of the drift gas on ion mobility can be evaluated quantitatively. For small ions near room temperature the mobility could be expressed using the following equation [Revercomb H. E.; Mason, E. A. "Theory of Plasma Chromatography/Gaseous Electrophoresis: A Review", Anal. Chem. 1975, 47, 970-983]:

$$K \cdot (\mu \cdot \alpha)^{1/2} \approx \text{const},$$

where $\alpha$ is the neutral polarizability, and for large ions ($\mu \approx M$):

$$K \cdot (M \cdot \alpha)^{1/2} \approx \text{const}.$$

Some quantitative evaluation of drift gas effects are summarized in table 2.

TABLE 2

| Drift gas | M, a.m.u. | $\alpha$, Å$^3$ | $(M \cdot \alpha)^{1/2}$ |
|---|---|---|---|
| He | 4.0 | 0.205 | 0.9 |
| Ar | 20.2 | 1.640 | 8.0 |
| N$_2$ | 28.0 | 1.760 | 7.0 |
| Kr | 83.8 | 2.480 | 14.4 |

Table 2 illustrates some quantitative evaluation of effects of drift gas change.

A wide range of variation in the mobility coefficient is observed with variations in drift gas composition. It should be also noted that an ion mobility changes in different gases due to as a result of the reduced mass term in the equation for the mobility coefficient. Using this, certain species that may overlap in conditions using one drift gas may be resolved in an atmosphere of a different drift gas.

To implement this technique for downhole/surface formation fluid analysis it is proposed to connect the ion mobility spectrometer to containers with different drift gases, e.g. nitrogen, helium, and air as shown in FIG. 2.

Simultaneous Identification of Negative and Positive Ions

Different components, depending on their chemical-physical properties and type of drift gas, will form negative or positive ions in the ionization part of the device, e.g.:

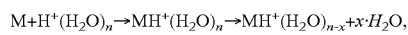

where M is the sample molecule, H$^+$(H$_2$O)$_n$ is the reactant ion, MH$^+$(H$_2$O)$_n$ is the cluster ion, MH$^+$(H$_2$O)$_{n-x}$ is the product ion;

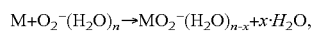

where O$_2^-$(H$_2$O)$_n$ is the negative reactant ion, MO$_2^-$(H$_2$O)$_{n-x}$ is the negative product ion.

Figure 3:
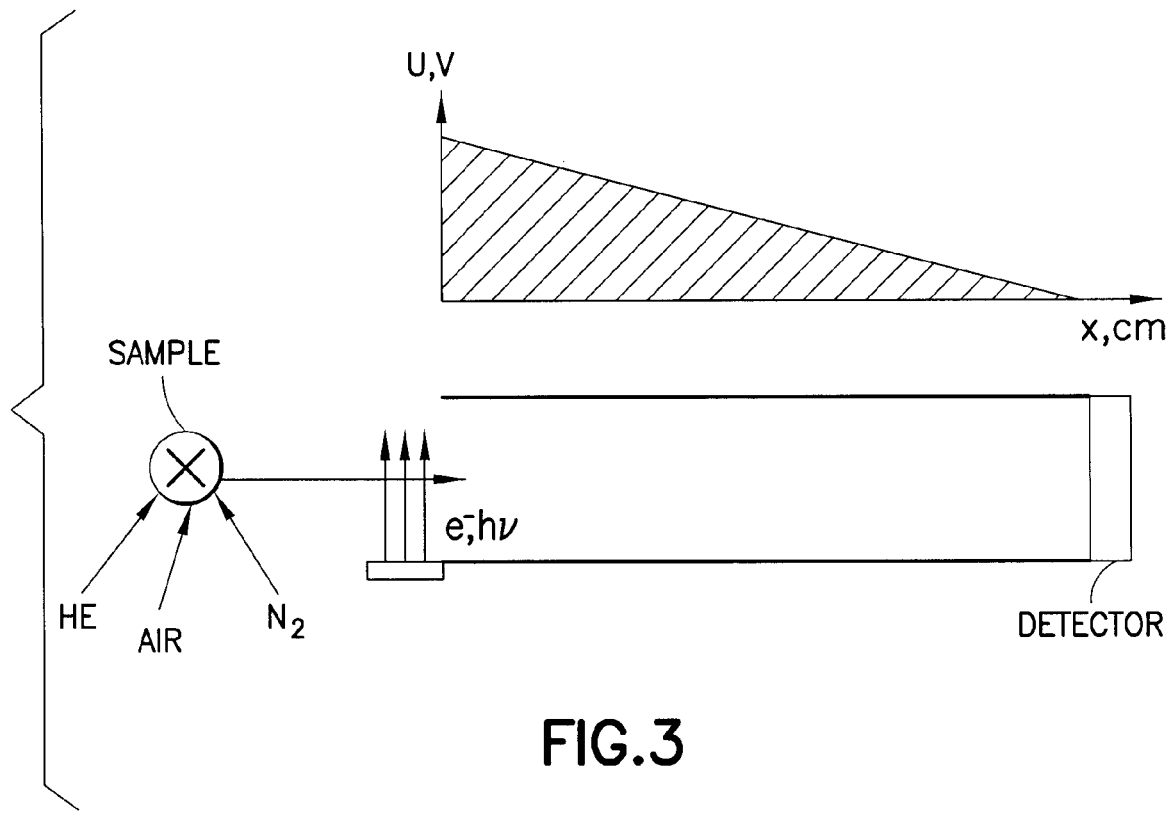
FIG. 3 shows the use of an ion mobility spectrometer to simultaneously detect ions of both polarities, according to embodiments of the invention.

Referring to FIG. 3, according to at least one aspect of the invention to simultaneously detect ions of both polarities it is proposed to use an ion mobility spectrometer. In this embodiment, the sample and drift gas are ionized either by a flux of electrons from a radioactive source (e.g. Ni$^{63}$) or by high energy photons (energy higher than 12.8 eV which is the ionization potential for CH$_4$). After ionization the negative and positive ions accelerate in the electric fields according to their polarities and are detected on opposite sides of the drift tube.

Figure 5:
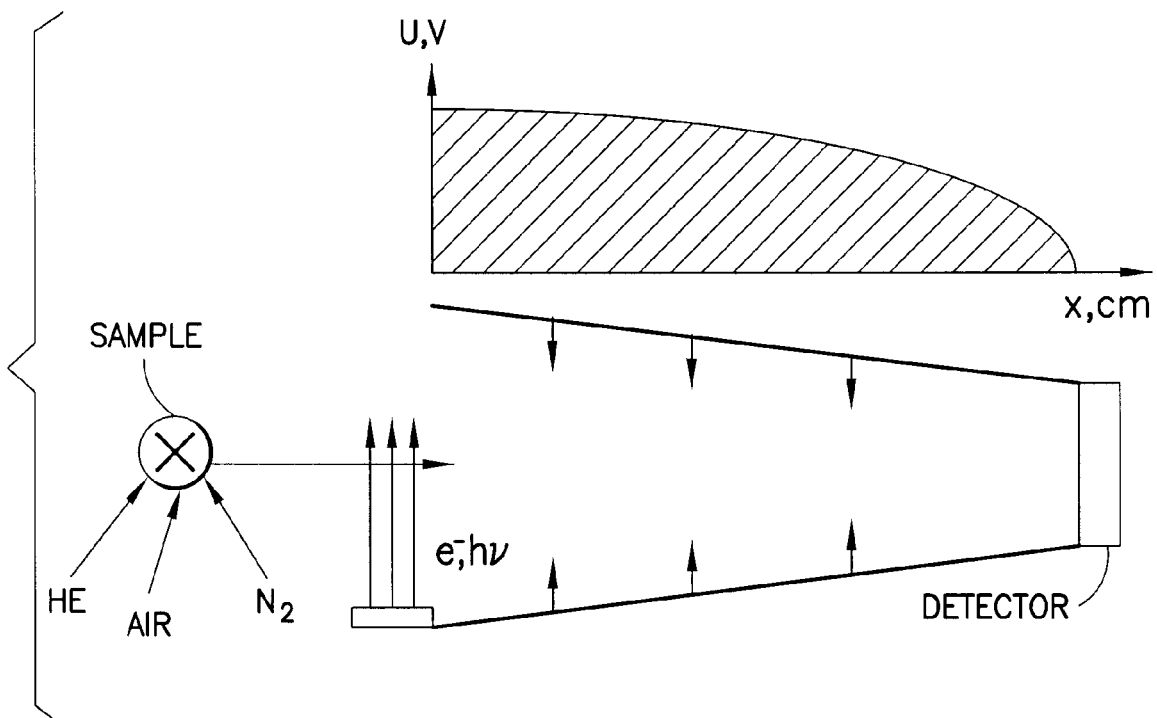
FIG. 5 shows at least one embodiment that can increase ion flux density as well as looks to avoid strong ion repulsion when ion density increases in the center of the drift tube, according to embodiments of the invention.
Figure 4:
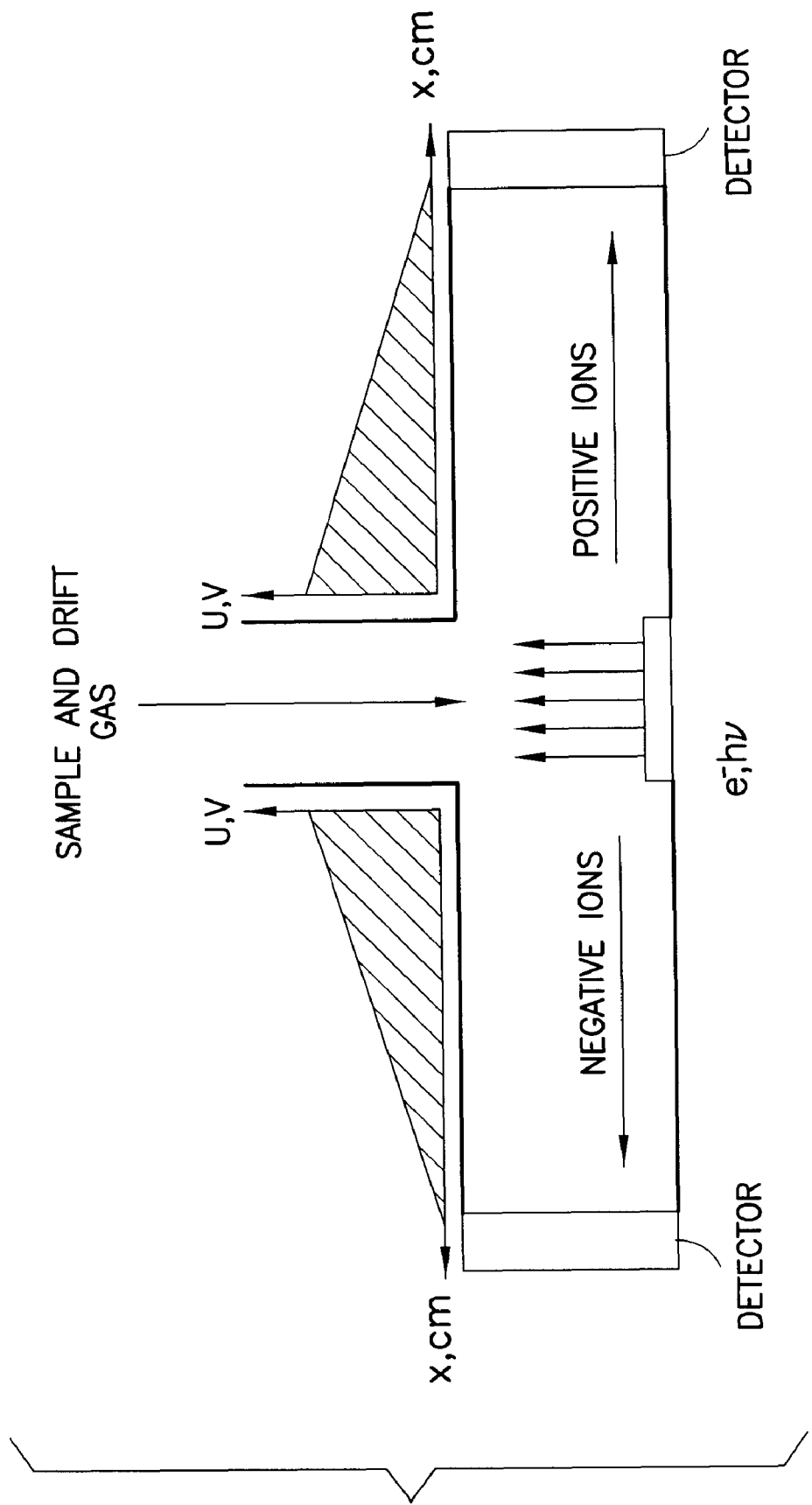
FIG. 4 shows at least one embodiment to increase ion flux density, according to embodiments of the invention.

Referring to FIGS. 4 and 5, in addressing the utilization of electrostatic field in the orthogonal direction to the drift tube, it is noted that the longitudinal diffusion increases the peak broadening in ion mobility spectrometry and correspondingly decreases the signal-to-noise ratio (SNR). It becomes especially important in the case of a high pressure experimental setup:

$$K = \frac{q \cdot D}{k \cdot T},$$

where D is the diffusion coefficient which is inversely proportional to the pressure in the drift tube. To increase ion flux density it is proposed to use the electrostatic field that is orthogonal to the drift tube axis electrostatic field with appropriate polarity. The band width in case of the drift tube with constant radius is increasing towards the end and it is appropriate to have a higher intensity electrostatic field toward the end of the drift tube. This can be accomplished either by varying the radius of the drift tube with a constant electrostatic field, e.g., see FIG. 4, or by increasing the field toward the end of the drift tube. At the same time, trying to avoid strong ion repulsion when ion density will increase in the center of the drift tube, it is proposed to utilize a nonlinear acceleration field along the drift tube (see FIG. 5). In the proposed embodiment the ion beam is shifted from the center of the drift tube (e.g. using ion optics) to increase signal-to-noise ratio.

Referring to FIG. 6, at least one embodiment of the invention proposes to address the utilization of M-sequence for ion-mobility measurements, for example the M-sequence [P. Z. Marmarelis and V. Z. Marmarelis, *Analysis of physiological systems*, Plenum Press, New York/London, 1978] can be used to improve signal-to-noise ratio (SNR) of ion mobility measurements. An M-sequence is a pseudo-random sequence of pulses $\alpha_i$ that assumes L different values, where L is the level of the sequence. In the example, L equal to 2 will be considered. Thus, the M-sequence will only assume two different values (1 and −1), as shown in FIG. 6. An auto-correlation function of M-sequence has a sharp peak:

$$\sum_{i=0}^{2^n-1} a_i \cdot a_{i+m} = 2^n \cdot \delta_m - 1,$$

and at the same time M-sequence almost do not correlate with any circular permutation of itself. The ratio between the minimal and maximum values of the correlation function is one over the length of the sequence. It also should be noted that M-sequence is orthogonal to the noise. It means that utilization of M-sequence increases the SNR level. If multiple copies of an M-sequence of duration τ are injected continuously into a drift tube (e.g. using Bradbury-Nielson ion gate), and a corresponding measurement of equal duration τ of the ion abundance is performed on the detector side, the detected signal will correspond to the injected sequence, circularly permuted by an amount equal to the drift time $t_d$ between ion injector and ion detector. Correspondingly, the cross-correlation function between the injected signal and the detected signal will peak sharply at $t_d$, thus allowing for precise measurement of the drift time.

Figure 7:
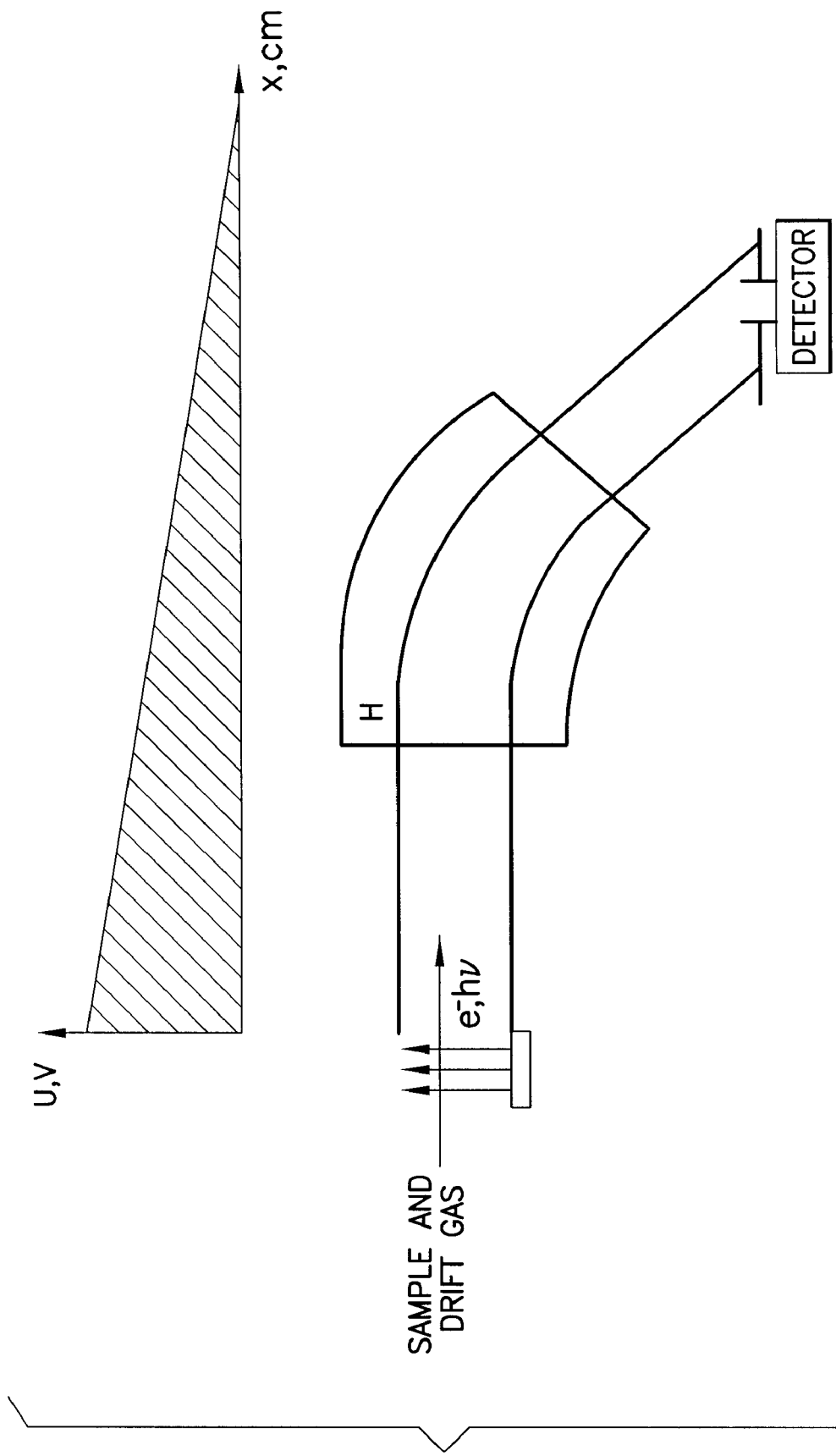
FIG. 7 shows when changing the Ionization Chemistry at least one method of the invention can include changing the selectivity of the DMS by controlling the ionization process, according to embodiments of the invention.

Referring to FIG. 7, as noted above, the magnetic sector mass spectrometer is one of the earliest mass spectrometer developed for component identification [C. Brunnee, *The*

*ideal mass analyzer: fact of fiction?, International Journal of Mass Spectrometry and Ion Processes,* 76 (1987), 125-237]. The utilization of a magnetic field provides for an additional mechanism that could be used for ion flux manipulation and improving the quality of analysis, for example increasing peak resolution. The implementation of a magnetic field will help to focus ions as well. The Lorentz describes the effect of magnetic field on ion flux in the drift tube:

$$q \cdot v \cdot B = \frac{m \cdot v^2}{R}. \qquad \text{Eq. (3)}$$

Substituting equations (1) and (2) in (3) and upon rearrangement, the radius of circular motion is obtained:

$$R = \frac{m}{q} \cdot \frac{K \cdot E}{B} = \frac{3 \cdot E}{16 \cdot N \cdot B \cdot \Omega} \cdot \left(\frac{2 \cdot \pi}{k \cdot T} \cdot \frac{m}{M} \cdot (m+M)\right)^{1/2}. \qquad \text{Eq. (4)}$$

From equation (4) it is seen that by varying the electrical or magnetic field it is possible to change the radius of ion flux and additionally resolve ions with different masses and cross-section of ion-neutral particle interaction.

At least one method of ionization, as noted above includes the method of differential ion mobility spectrometry (DMS). For example, DMS can utilize a variety of ionization sources including radioactive ionization, corona discharge ionization, capacitive discharge ionization, and UV photo-ionization (the most common being $^{63}$Ni). Both positive and negative reactant ions react through proton transfer and charge transfer to generate analyte ions. The reactant ion pool in the case of DMS is largely composed of proton-water-nitrogen clusters for the positive ions, and oxygen anion-water clusters for the negative ions (Eiceman, G., Karpas, Z. *Ion Mobility Spectrometry*, CRC Press, Boca Raton, Fla., 1993), similar to the ionization process described for IMS.

When changing the Ionization Chemistry according to an aspect of the invention, at least one method can include changing the selectivity of the DMS by controlling the ionization process. The process of atmospheric pressure chemical ionization is still largely not understood within the science arena. It has, however, been demonstrated that by biasing the ionization towards a certain species, more accurate measurements of a specific species in a complex matrix can be achieved (Lawrence, A. H., Neudorfl, P. *"Detection of Ethylene Glycol Dinitrate vapors by Ion Mobility Spectrometry Using Chloride Reagent Ions"*, Anal. Chem. 1988, 60, 104-109). A method to produce such an effect can be imagined by changing the chemical composition of the gas in the ionization region of the detector. This can be done either, by changing chemical composition of the carrier gas or the transfer gas, as long it is done before the ionization region. The resulting effect is that the reactant ion pool will consist of different ionizing species, changing the ionizability of the sample by the reactant ion. There are several methods that could be used for such a scenario including but not limited to introduction of this chemical substituent directly in the carrier gas, or through diffusion tubes or gas mixing from multiple sources in the system.

In the case of varying drift gases, ion mobility can be governed similarly to that which was explained above for IMS. Most commonly a single drift gas can be used to transportions through the filter region of a DMS. Changing the mobility of an ion in the field can be manipulated using equation 2 (see above). Depending on how the mobility of specific ions change, the transport gas, or a mixture of gases can be used to isolate those ions for detection.

Negative ion detection in DMS is most often a result of fragmentation of the parent molecule to yield a halogen ion. The negatively charged species traverse the ion filter region in the same manner as positive ions and reach a biased collector plate. The most common ion sources in IMS/DMS are the $^{63}$Ni and a photoionization source (UV lamp). For many halogenated species the electron energy can fragment a halide ion resulting in the formation of both positive and a negative daughter species. Commonly the negative daughter species is the fragmented halogen ion. For a homologous series of components containing a halogen it can be expected that once fragmented, the negative ion will be detected at a defined compensation voltage for the Cl-, Br-, and I-ions respectively. (Dissociation energy of C—Cl bond is 3.8 eV, C—Br—2.8 eV). Similar behavior has been documented for acetate containing species on the positive channel. Instrumental parameters can be controlled to monitor for a specific functional group amenable to fragmentation under DMS operating conditions (in the case of halogenated species or acetates).

Figure 8:
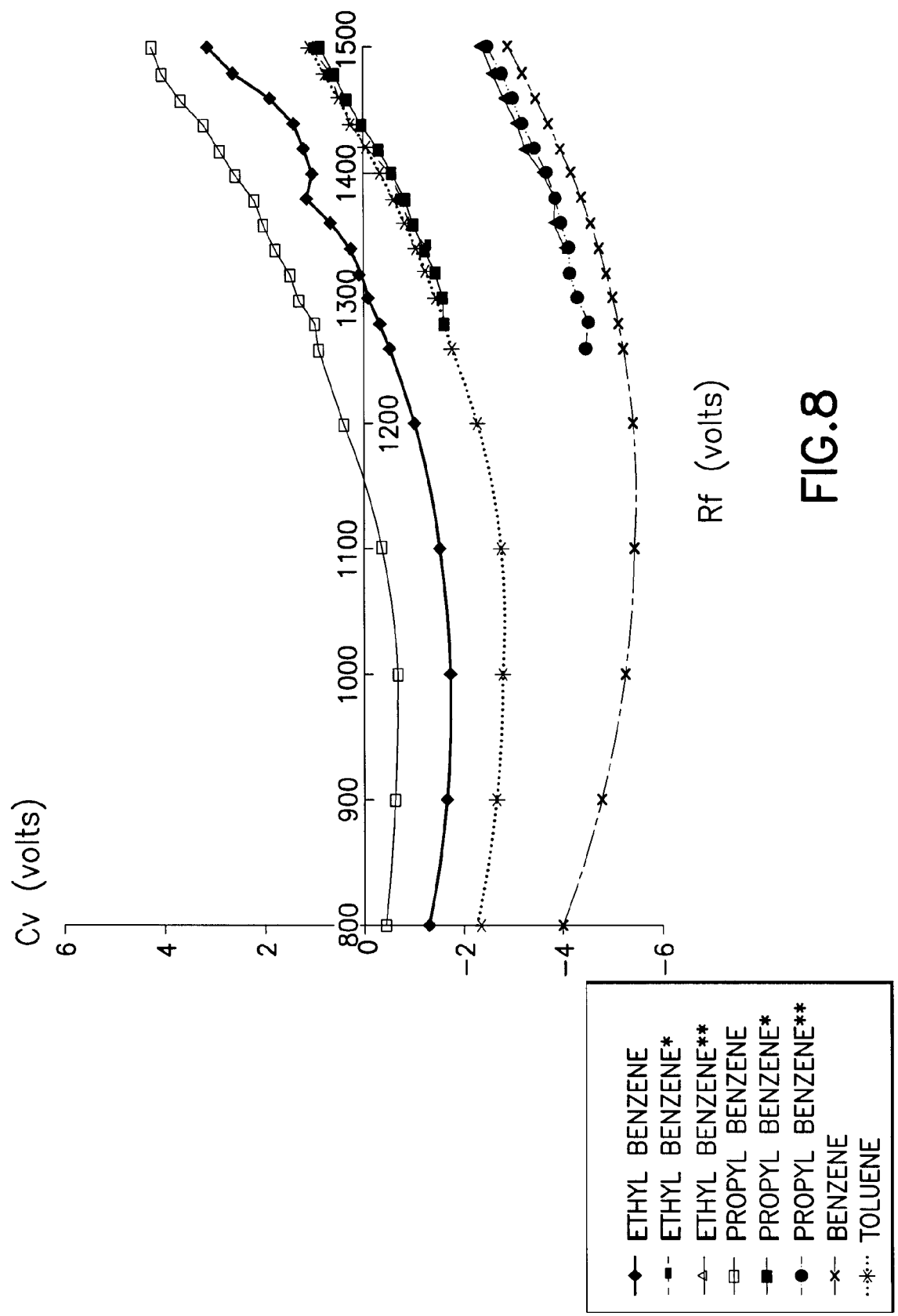
FIG. 8 shows that by changing the ionization source (higher energy) or the operating conditions of the DMS it is possible to induce fragmentation in many sample species, according to embodiments of the invention.

According to an aspect of the invention and referring to FIG. 8, it is noted that by changing the ionization source (higher energy) or the operating conditions of the DMS it is possible to induce fragmentation in many sample species. Collision induced dissociation (controlled by operating parameters) has also been suggested as a possible avenue to generate fragmented species in DMS. The instrumental control conditions under which a component fragments can be utilized only after calibration for each component of interest. This allows for control of conditions in which the fragmentation may take place. Fragmentation data for a set of alkyl substituted aromatics is shown in FIG. 8. The plot of compensation voltage versus field strength indicates that fragmentation of these ions only occurred under conditions where the Rf voltage applied was greater than ~1250 volts. The data shows that for ethyl- and propyl-benzene, daughter ions that closely matched the mobility traces for benzene and toluene were generated.

For example, in the case of higher molecular weight components, where mobilities tend to span a very narrow range, fragmentation can be particularly useful. In these cases the fragmented species most likely would have significantly higher mobilities (than the parent ions) and the separation and detection of these fragments relative to other parent ions will be much simpler. The fragmentation of the parent ions then provides several avenues for exploitation of the mobility data. Fragmentation patterns collected during an analysis can be matched to libraries for component identification similar to mass spectral databases. Furthermore, the presence of a specific daughter ion can be used as an indicator of the parent molecule structure, and this type of information can aid in characterization of mixture constituents. This type of data suggests that DMS-DMS techniques, analogous to MS-MS techniques, can be used for structural identification of unknown components (Kendler, S., Lambertus, G. R., Dunietz, B. D., Coy, S. L., Nazarov, E. G., Miller, R. A., Sacks, R. A., *"Fragmentation patterns and mechanisms of aromatic compounds in atmospheric pressure studied by GC-DMS and DMS-MS,"* Int. J. of Mass, Spectrom. 2007, 263, 137-147).

Figure 9:
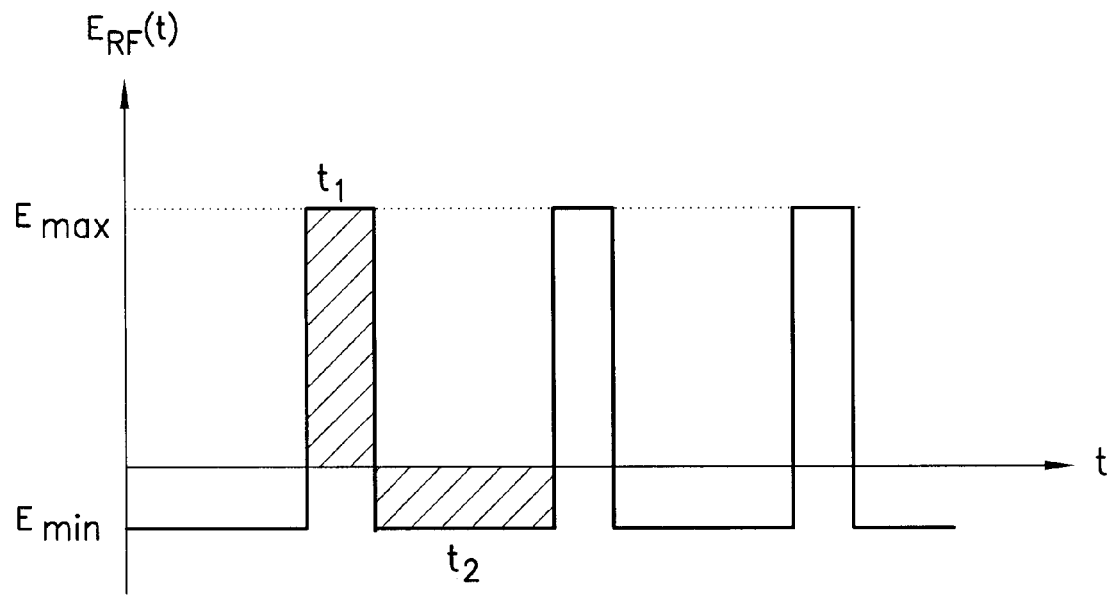
FIG. 9 shows a waveform describing an alternating electric field in DMS according to embodiments of the invention.

According to aspects of the invention and referring to FIG. 9, the invention addresses the variation in the high-frequency field, for example, the electric field in DMS can be generated by applying a high frequency RF voltage and a low DC voltage to two parallel plate electrodes. The invention provides for a simplified waveform as shown in FIG. 9, where the maximum field strength, $E_{max}$, is less than 10000 V/cm, and the minimum field strength, $E_{min}$, is much less than $E_{max}$. The waveform is designed so that the time averaged electric field is zero, or $$|E_{max}| \cdot t_1 - |E_{min}| \cdot t_2 = \beta,$$

where $t_1$ is the portion of the period where the high field is applied, $t_2$ is the portion where the low field is applied, and $\beta$ is a constant corresponding to the area under the curve.

Figure 10:
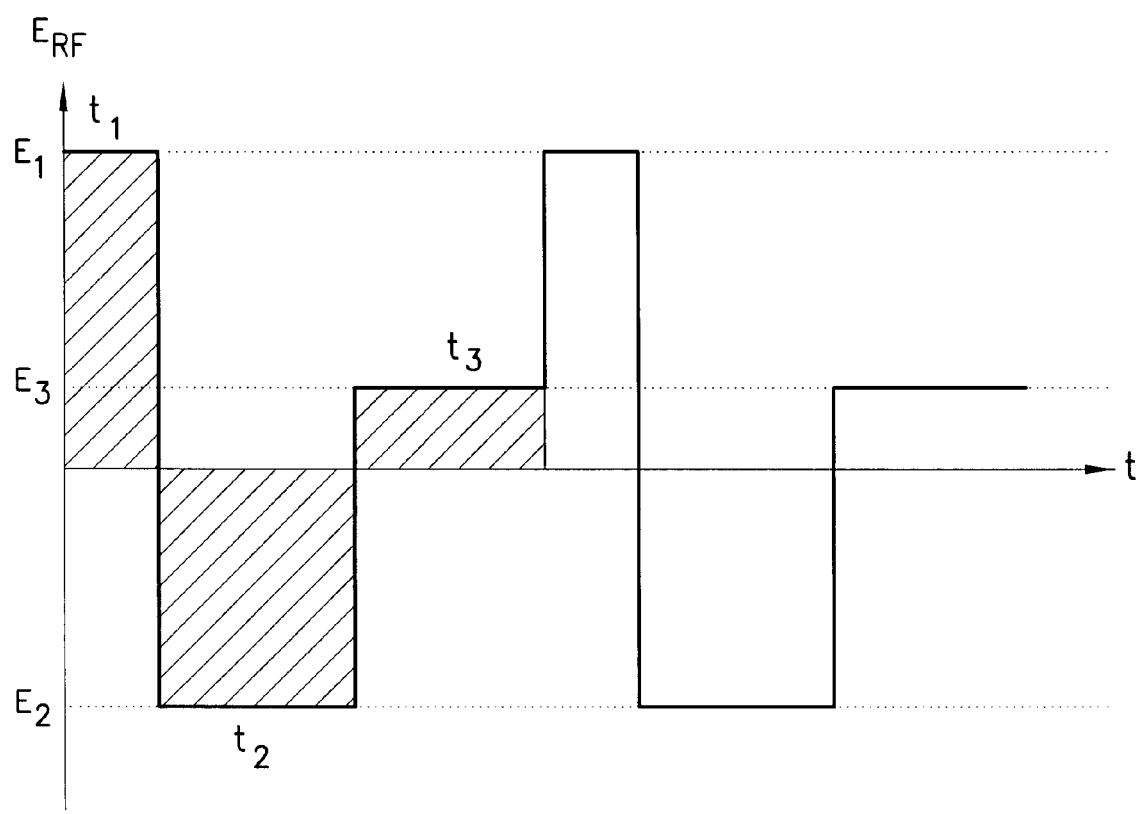
FIG. 10 shows a waveform describing a higher order alternating electric field, according to embodiments of the invention.

Ions in the tunable ion filter region of the DMS experience this alternating electric field and oscillate orthogonal to the direction of carrier gas flow. The ion velocity in the transverse direction is described by equation 1:

$$v_y = K \cdot E$$

where K is the mobility of the ion and E is the electric field strength. The mobility of the ion depends on the electric field according to:

$$K(E) = K_0(0)[1 + \alpha_2 (E/N)^2 + \alpha_4 (E/N)^4 + \alpha_6 (E/N)^6 + \dots] \quad \text{Eq. (5)}$$

where N is the density of the carrier gas, and $\alpha_n$ indicates a coefficient in a series expansion. In practice, IMS separations are done under conditions with zero field mobility in the y-direction, and only the $K_0(0)$ term plays a role. For the case of DMS with high electric field strengths, the higher order terms $(E/N)^2$ and $(E/N)^4$ in the equation become more significant. Ion displacement from the original position can't then be measured as:

$$\Delta y = v_y \cdot \Delta t$$

where $\Delta t$ is the length of time the field is applied. After substation displacement of the ion over a single RF cycle can be calculated as $$\Delta y = \beta \cdot (K_1 - K_2)$$

where $K_1$ and $K_2$ are the mobilities for the high and low field respectively. To make use of the higher order terms in the mobility series, imagine expanding the waveform to have more than a single $E_{max}$ and $E_{min}$ per cycle, for example see FIG. 10.

In this case, the description of the waveform is as follows, $$|E_1| \cdot t_1 + |E_3| \cdot t_3 - |E_2| \cdot t_2 = \beta$$

and the displacement over one period of the RF cycle is, $$\Delta y = K_1 \cdot |E_1| \cdot t_1 + K_3 \cdot |E_3| \cdot t_3 - K_2 \cdot |E_2| \cdot t_2$$

which simplifies to $$\Delta y = \beta \cdot (K_1 + K_3 - K_2)$$

For this situation, the displacement of each ion will be different relative to the case with only a single $E_{max}$ and $E_{min}$ due to resulting changes in ion mobility during each portion of the RF cycle. Operating under these conditions will create a new mobility value for each ion. For the situation where a measurement of a specific species in a complex matrix is desired, the RF cycle can be manipulated until that ion has a unique mobility. Selected mobility monitoring will then allow for the best signal to noise measurement of that ion. There are infinite combinations of RF cycles that can be employed. To further this, DMS-DMS instruments can be employed where each successive DMS has a different RF cycle to generate complimentary information to describe a specific ion.

Figure 11:
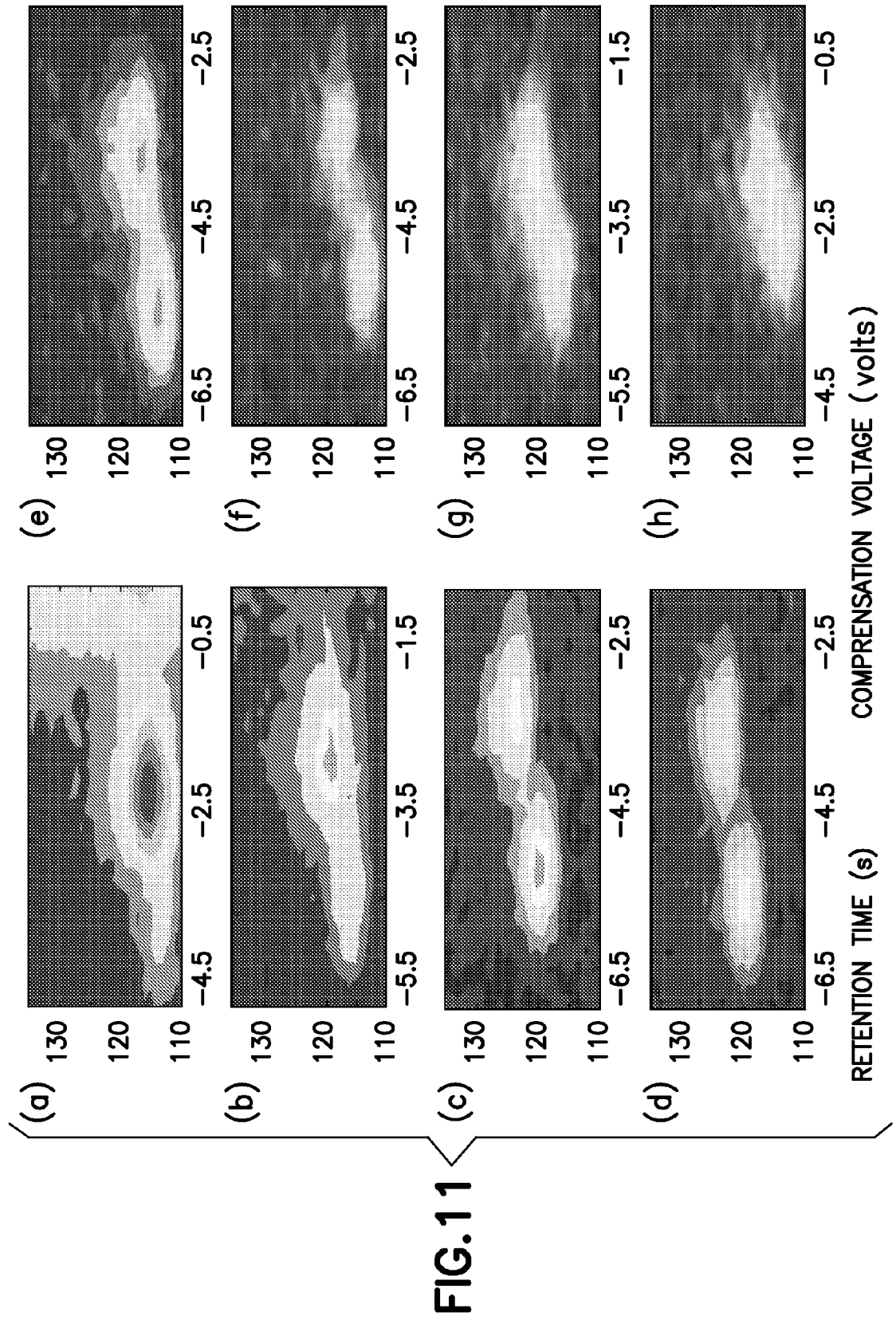
FIG. 11 shows Contour plots for 3-methyl-2-butanone and benzene for RF voltages of 800 V (a), 900 V (b), 1000 V (c), 1100 V (d), 1200 V (e), 1300 V (f), 1400 V (g) and 1500 V (h), wherein the left peak is benzene and the right peak is 3-methyl-2-butanone and the detector temperature is 100° C.

According to aspects of the invention, the invention provides for a method for programming the electric field. For example, FIG. 11 illustrates the resolution in terms of the separation space along the compensation voltage axis of a differential mobility spectrometer has been previously measured through analogy to peak capacity measurements in gas chromatography (Lambertus, G. R., Fix, C. S., Reidy, S. M., Miller, R. A., Wheeler, D., Nazarov, E., Sacks, R. D. "*Silicon Microfabricated Column with Microfabricated Differential Mobility Spectrometer for GC Analysis of Volatile Organic Compounds,*" Analytical Chemistry, 2005, 77(23), 7563-7571). This work demonstrated the ability to control resolution of two components that coelute from a chromatographic column by selectively tuning the strength of the electric field for a set of components, for example see FIG. 11. Known DMS technology relies on inputting a single Rf voltage amplitude to determine the strength of the electric. Then a scan of a range of compensation voltages to measure the mobility of a range of ions can be done. However, according to an aspect of the invention it is suggested that a method of improving the resolution in terms of the separation space available can be achieved through scanning a range of electric field strengths real-time during an analysis. For example, scanning alternating field strength either could be done while maintaining a single compensation voltage, or while scanning a range of compensation voltages. By changing the field, the field dependence on the mobility of an ion will change with equation (5). The changing mobility with changing field strength will change the mobility of the targeted species, and ideally will shift the mobility of the species in a manner that makes detection of both species possible.

Another aspect of the invention, the invention can reduce gas consumption. For example, gas consumption is traditionally considered a problem when utilized outside the laboratory due to its portability and usage in difficult environments, e.g., in the field. In particular, transport gas consumption in DMS systems is approximately on the order of 250-400 mL/min of clean dry gas. This amount of consumable gas is problem in the field and/or downhole environments where transporting of such consumables is complex and expensive. Re-circulating pumps and filters have been explored as a possible alternative to the high cost of transporting gas, but the issue of replacing filters then arises. However, according to aspects of the invention, there is at least one other possible method of reducing transport gas consumption which may include for example, reducing the length of the ion filter region. The carrier gas consumption is set out of necessity in an effort to reduce ion residence time in the ion filter region. Restricting transport gas consumption, residence time of ions in this region will increase, the alternating electric field would result in all ions hitting the electrodes and being neutralized. Further, the balance in transport gas flow also requires that molecules spend enough time in the ionization region that a good portion of them are ionized, so the balance is ionization versus neutralization.

According to another aspect of the invention, the invention can alleviate some of the gas consumption problems as noted above by changing the geometry of the electrodes. For example, by shortening the length of the electrodes, a decrease in volumetric flow rate will maintain the residence time requirements in the filter region.

Figure 12:
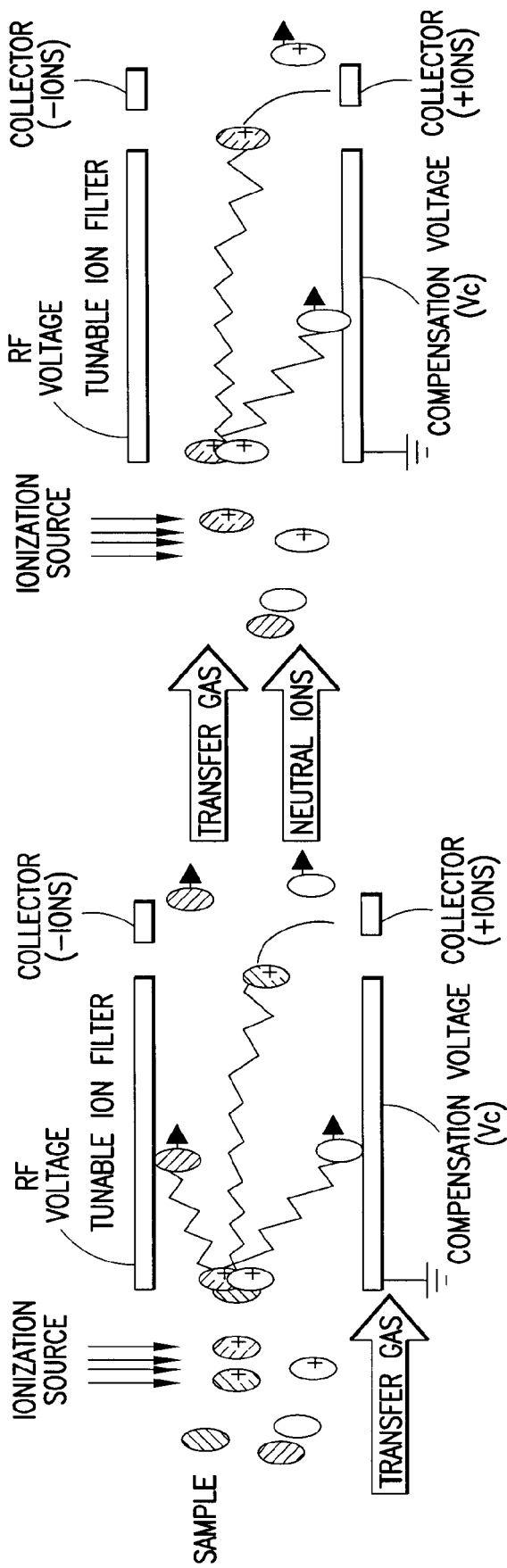
FIG. 12 shows at least one conceptual image of multiplexed DMS, according to embodiments of the invention.

Another aspect of the invention includes multiplexed or arrayed DMS as shown in FIG. 12. For example, differential mobility spectrometers operating in scanning modes are often limited to relatively slow sampling rates, limited by step settling times when the compensation voltage is changed. Also, as previously mentioned the ability to scan a range of alternating field strengths would help to enhance resolution along the compensation voltage axis. This works by providing conditions at which ions mobility will shift independently of other ions (present in the ion filter region at the same time) in such a manner that independent detection is possible. Multiplexed DMS offers a possible to solution to both problems.

A possible configuration would most simplistically consist of two or more DMS units connected end to end, where effluent from the first cell flows into the second, as shown in FIG. 12.

Such an arrangement of spectrometric detectors would allow for each successive filter to have different compensation voltage settings, different compensation voltage scan ranges, different field strengths, different field strength scan ranges, or can have the same settings but be used to improve the time resolution of the measurements. A configuration where different ion sources are used is another implementation where selective ionization and detection can take place in several steps enhancing data output from a single measurement.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, while some of the embodiments described herein refer to time-of-flight Ion Mobility Spectrometry (IMS) and differential mobility spectrometry (DMS) that can allow for a selective marker-free identification of molecules and molecular aggregates in a mixture that can be used as a detector for gas/liquid chromatography and other compositional analysis systems like a mass spectrometry. This invention may also be coupled with a pre-separation apparatus such as GC or LC as well as with a device for accurate component identification like MS. Further, it is also possible to improve the ion separation, such that the ion mobility spectrometers could be combined in a tandem like IMS-IMS, IMS-DMS and so on. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for chemically analyzing at least one sample of fluid, the method comprising the steps of:
   a) directing a gas flow of the at least one fluid sample into a mixing region of an ion mobility device, wherein the mixing region is in communication with at least one container having at least one other fluid;
   b) creating an ion flow of gaseous ions, a mixture of gaseous ions or a gaseous neutral species from the at least one sample and the at least one other fluid; and
   c) injecting the ion flow from the mixing region into at least one ion mobility assembly of the ion mobility device, the at least one ion mobility assembly comprising at least one mobility tube; and, detecting the ions from the ion flow exiting the ion mobility assembly.

2. The method of claim 1, wherein the at least one sample of fluid is collected from one or more inlet location where the fluids originated.

3. The method of claim 1, wherein the ion mobility device includes one or more sampling chamber.

4. The method of claim 3, wherein the at least one fluid sample is directed into the one or more sampling chamber of the ion mobility device wherein the one or more sampling chamber provides for the at least one fluid sample to be put in a gaseous phase so as to create the gas flow of step (a).

5. The method of claim 3, wherein at least one device is structured and arranged between the at least one sample chamber and the mixing region, such that the at least one device is from the group consisting of one of a separation system, a non-destructive sensor, a mass spectrometer, another ion mobility device, or some combination thereof.

6. The method of claim 5, wherein the separation system includes one of a liquid chromatography, a gas chromatography, a size exclusion chromatography system, or some combination thereof.

7. The method of claim 1, wherein the at least one other fluid consist of one or more drift gas.

8. The method of claim 7, wherein the one or more drift gas is from the group consisting of one of nitrogen, helium, air, argon, water vapor, one or more organic molecules, one or more inorganic molecules or any combination thereof.

9. The method of claim 1, wherein the at least one sample and the at least one other fluid are ionized from a group consisting of one of a flux of electrons from a radioactive source, by high energy photons with an energy higher than 12.8 eV, a gas discharge device, an ion flux system, a field ionization assembly, a penning ionization process, a chemical ionization assembly, a dissociative ionization assembly, a collision induced ionization assembly or some combination thereof.

10. The method of claim 1, wherein the at least one ion mobility assembly includes a top electrode and a bottom electrode, such that ion flow is injected into a filter region of the at least one mobility tube by one of orthogonally or parallel in relation to an axis of the bottom electrode.

11. The method of claim 1, wherein the at least one mobility tube includes a filter region comprising of two or more electrodes along with at least one inlet positioned on an end of the at least one mobility tube.

12. The method of claim 11, wherein the filter region has a filter geometry wherein two electrodes of the two or more electrodes are spaced apart from each other, such that an inlet cross-section is greater than an exit cross-section.

13. The method of claim 11, wherein the filter region has a filter geometry wherein two electrodes of the two or more electrodes are spaced apart from each other, such that an inlet cross-section is less than an exit cross-section.

14. The method of claim 11, wherein the filter region has a filter geometry wherein two electrodes of the two or more electrodes are non-uniformly spaced apart from each other, such that an inlet cross-section is greater than an exit cross-section.

15. The method of claim 11, wherein the filter region has a filter geometry wherein at two electrodes of the two or more electrodes are non-uniformly spaced apart from each other, such that an inlet cross-section is less than an exit cross-section.

16. The method of claim 1, wherein the at least one mobility tube includes at least one inlet positioned between a first end and a second end of the at least one mobility tube.

17. The method of claim 16, wherein the filter region has a filter geometry wherein two electrodes of the two or more electrodes are uniformly spaced apart from each other.

18. The method of claim 1, wherein the at least one mobility tube includes a filter region, such that the filter region is positioned downstream from step (c) or an ionization region.

19. The method of claim 1, wherein the at least one ion mobility assembly simultaneously detects ions of both negative and positive polarities.

20. The method of claim 19, wherein the at least one sample and the at least one other fluid are ionized, after ionization a plurality of negative and positive ions accelerate in at least two electric fields according to their respective ion polarities and are detected on opposite sides of at least one mobility tube of the plurality of mobility tubes.

21. The method of claim 1, wherein the ion mobility device has two or more ion mobility assemblies.

22. The method of claim 1, wherein the at least one ion mobility assembly has two or more detectors.

23. The method of claim 1, wherein the at least one fluid from the fluids is from the group consisting of one of a formation fluid mixture or a fluid from an oilfield application.

24. The method of claim 1, wherein the fluids are one of formation fluids or fluids from the mixing region or some combination thereof.

25. The method of claim 24, wherein the formation fluids are from a group consisting of one of water, crude oil, drilling mud, gases or any combination thereof.

26. The method of claim 24, wherein the fluids from the mixing region are from the group consisting of one of gases, inorganic dopant, organic dopant, water vapor or any combination thereof.

27. The method of claim 1, wherein ion mobility device is from the group consisting of one of a ion mobility spectrometry or a differential ion mobility spectrometry.

28. The method of claim 1, further comprises:
   recording the results of the detected ions by the at least one ion mobility assembly into a processor as an ion mobility spectral profile data;
   inputting other measured data from other well log systems into the processor;
   analyzing the combination of the ion mobility spectral profile data with the other measured data by conducting one of a quantitative analysis, a qualitative analysis or both a quantitative and qualitative analysis so as to provide reliable reservoir evaluation information for making a decision in relation to oilfield applications.

29. A method for chemical analysis of fluids from an oilfield application such as a reservoir, the method comprising:
   a) collecting at least one sample of fluid from one or more inlet location where the fluids originated, and an ion mobility device having one or more sampling chamber and at least one ion mobility assembly;
   b) directing the at least one fluid sample into the one or more sampling chamber of the ion mobility device wherein the one or more sampling chamber provides for the at least one fluid sample to be put in a gaseous phase so as to create a gas flow;
   c) directing the gas flow of the at least one fluid sample into a mixing region of the ion mobility device, wherein the mixing region is in communication with at least one container having at least one other fluid;
   d) creating an ion flow of gaseous ions, a mixture of gaseous ions or a gaseous neutral species from the at least one sample and the at least one other fluid; and
   e) injecting the flow from the mixing region into the at least one ion mobility assembly of the ion mobility device, the at least one ion mobility assembly comprising at least one mobility tube; and, detecting the ions from the flow exiting the at least one ion mobility assembly.

30. A ion mobility device, the ion mobility device comprising:
   a mixing region is in fluid communication with a first fluid of at least one fluid sample and one or more container having at least one other fluid, such that the first fluid is mixed with the at least one other fluid;
   a source for generating a flow of gaseous ions, a mixture of gaseous ions or a gaseous neutral species from the at least one fluid sample and the at least one other fluid;
   at least one ion mobility assembly fluidly connected to the source, the at least one ion mobility assembly comprising at least one mobility tube and at least one detector, wherein the at least one ion mobility assembly is detecting ions from an ion flow exiting the ion mobility assembly.

31. The ion mobility device of claim 30, wherein the first fluid of the at least one fluid sample is in fluid communication with one or more sample chamber.

32. The ion mobility device of claim 31, wherein the one or more sample chamber provides for the first fluid of the at least one fluid sample to be put in a gaseous phase so as to create a gas flow.

33. The ion mobility device of claim 32, wherein the at least one other fluid consists of one or more drift gas.

34. The ion mobility device of claim 33, wherein the one or more drift gas is from the group consisting of one of nitrogen, helium, air, argon, water vapor, one or more organic molecules, one or more inorganic molecules or any combination thereof.

35. The ion mobility device of claim 30, wherein the at least one mobility tube includes a filter region comprising of two or more electrodes along with at least one inlet positioned on an end of the at least one mobility tube.

36. The ion mobility device of claim 35, wherein the filter region has a filter geometry wherein two electrodes of the two or more electrodes are spaced apart from each other, such that an inlet cross-section is greater than an exit cross-section.

37. The ion mobility device of claim 35, wherein the filter region has a filter geometry wherein two electrodes of the two or more electrodes are spaced apart from each other, such that an inlet cross-section is less than an exit cross-section.

38. The ion mobility device of claim 35, wherein the filter region has a filter geometry wherein two electrodes of the two or more electrodes are non-uniformly spaced apart from each other, such that an inlet cross-section is greater than an exit cross-section.

39. The ion mobility device of claim 35, wherein the filter region has a filter geometry wherein two electrodes of the two or more electrodes are non-uniformly spaced apart from each other, such that an inlet cross-section is less than an exit cross-section.

40. The ion mobility device of claim 30, wherein the at least one mobility tube includes at least one inlet positioned between a first end and a second end of the at least one mobility tube.

41. The ion mobility device of claim 40, wherein the filter region has a filter geometry wherein two electrodes of the two or more electrodes are uniformly spaced apart from each other.

42. The ion mobility device of claim 30, wherein the at least one mobility tube includes a filter region, such that the filter region is positioned downstream from step (c) or the ionization region.

43. The ion mobility device of claim 30, wherein the at least one ion mobility assembly includes a top electrode and a bottom electrode, such that ion flow is injected into a filter region of the at least one mobility tube by one of orthogonally or parallel in relation to an axis of the bottom electrode.

44. The ion mobility device of claim 30, wherein at least one device is structured and arranged between the at least one sample chamber and the mixing region, such that the at least one device is from the group consisting of one of a separation system, a non-destructive sensor, a mass spectrometer, another ion mobility device, or some combination thereof.

45. The ion mobility device of claim 44, wherein the separation system includes one of a liquid chromatography, a gas chromatography, a size exclusion chromatography system, or some combination thereof.

46. The ion mobility device of claim 30, wherein the at least one ion mobility assembly simultaneously detects ions of both negative and positive polarities.

47. The ion mobility device of claim 30, wherein the ion mobility device has two or more ion mobility assemblies.

48. The ion mobility device of claim 30, wherein the at least one ion mobility assembly has two or more detectors.

49. The ion mobility device of claim 30, wherein the at least one ion mobility device uses a plurality of electrostatic fields to focus ion flux in the at least one mobility tube to effect a peaks resolution and a signal to noise ratio.

50. The ion mobility device of claim 30, wherein the at least one ion mobility device includes at least one magnetic field that is used for ion flux manipulation to improve one or more component of interests resolutions in the analyzable mixture of the first fluid with the at least one other fluid.

51. The ion mobility device of claim 30, wherein a m-sequence ion injection is used to enhance a signal to noise ratio and resolution between the one or more components of interests in ion mobility measurements.

52. The ion mobility device of claim 30, wherein the at least one ion mobility device includes multiplexing ion mobility spectrometry cells, such that an array of sensors are arranged in parallel rather in series, along with the at least one sample being introduced as a continuous flow to an ionization source, a filter region, and a plurality of collectors as the at least one sample is transported by means of a transfer gas.

53. The ion mobility device of claim 30, wherein ion mobility device is from the group consisting of one of an ion mobility spectrometer or differential ion mobility spectrometer.

54. The ion mobility device of claim 30, wherein ion mobility device operates above an ambient pressure and an ambient temperature.

55. The ion mobility device of claim 30, wherein the at least one ion mobility assembly has one or more electric field, such that the one or more electric field oscillating is with one of one or more maximum pulses, one or more minimum pulses or both.

56. A system for chemical analysis of fluids from an oilfield application such as a reservoir, the system comprising:
   a) collecting at least one sample of fluid from one or more inlet location where the fluids originated, and an ion mobility device having one or more sampling chamber and at least one ion mobility assembly;
   b) directing the at least one fluid sample into the one or more sampling chamber of the ion mobility device wherein the one or more sampling chamber provides for the at least one fluid sample to be put in a gaseous phase so as to create a gas flow;
   c) directing the gas flow of the at least one fluid sample into a mixing region of the ion mobility device, wherein the mixing region is in communication with at least one container having at least one other fluid;
   d) creating an ion flow of gaseous ions, a mixture of gaseous ions or a gaseous neutral species from the at least one sample and the at least one other fluid; and
   e) injecting the flow from the mixing region into the at least one ion mobility assembly of the ion mobility device, the at least one ion mobility assembly comprising at least one mobility tube; and, detecting the ions from the flow exiting the at least one ion mobility assembly.

* * * * *